US009011849B2

(12) United States Patent
Tamaki

(10) Patent No.: US 9,011,849 B2
(45) Date of Patent: Apr. 21, 2015

(54) AMELIORATING OR THERAPEUTIC AGENT FOR CHRONIC PROSTATITIS, INTERSTITIAL CYSTITIS AND/OR URINATION DISORDERS

(75) Inventor: Makoto Tamaki, Fukushima (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/583,408

(22) PCT Filed: Mar. 10, 2011

(86) PCT No.: PCT/JP2011/055609
§ 371 (c)(1),
(2), (4) Date: Sep. 7, 2012

(87) PCT Pub. No.: WO2011/111770
PCT Pub. Date: Sep. 15, 2011

(65) Prior Publication Data
US 2013/0028982 A1    Jan. 31, 2013

(30) Foreign Application Priority Data

Mar. 11, 2010  (JP) ................................ 2010-054626
Apr. 23, 2010  (JP) ................................ 2010-100234

(51) Int. Cl.
   *A61K 39/285*   (2006.01)
   *A61K 39/295*   (2006.01)
   *A61K 39/00*    (2006.01)
   *A61K 35/36*    (2006.01)

(52) U.S. Cl.
   CPC ........... *A61K 35/36* (2013.01); *A61K 2039/515* (2013.01)

(58) Field of Classification Search
   USPC ...................................... 424/130.1, 520, 572
   See application file for complete search history.

(56) References Cited

U.S. PATENT DOCUMENTS

| | | | |
|---|---|---|---|
| 4,985,254 A | 1/1991 | Konishi | |
| 5,013,558 A | 5/1991 | Konishi | |
| 5,057,324 A | 10/1991 | Shibayama et al. | |
| 5,534,509 A | 7/1996 | Konishi et al. | |
| 5,560,935 A | 10/1996 | Konishi et al. | |
| 6,051,613 A | 4/2000 | Ohno et al. | |
| 6,165,515 A | 12/2000 | Matsuyama et al. | |
| 6,238,665 B1 | 5/2001 | Naiki | |
| 6,251,929 B1 | 6/2001 | Naiki et al. | |
| 6,365,192 B1 | 4/2002 | Konishi | |
| 6,440,978 B2 | 8/2002 | Yoshii et al. | |
| 6,451,831 B1 | 9/2002 | Ienaga et al. | |
| 7,148,012 B2 | 12/2006 | Nishioka | |
| 7,148,121 B2* | 12/2006 | Houston | 438/455 |
| 7,238,487 B2 | 7/2007 | Nishioka | |
| 7,435,547 B2 | 10/2008 | Nishioka | |
| 8,293,280 B2 | 10/2012 | Ansari et al. | |
| 8,338,108 B2 | 12/2012 | Nakamura et al. | |
| 2006/0051376 A1 | 3/2006 | Nishioka | |
| 2006/0134646 A1 | 6/2006 | Ansari et al. | |
| 2006/0263388 A1 | 11/2006 | Nishioka | |
| 2007/0218037 A1 | 9/2007 | Nishioka | |
| 2011/0111051 A1 | 5/2011 | Oishi et al. | |
| 2012/0135083 A1 | 5/2012 | Kurohashi et al. | |

FOREIGN PATENT DOCUMENTS

| | | |
|---|---|---|
| JP | 53-101515 A | 9/1978 |
| JP | 55-87724 A | 7/1980 |
| JP | 1-265028 A | 10/1989 |
| JP | 1-319422 A | 12/1989 |
| JP | 2-28119 A | 1/1990 |
| JP | 7-97336 A | 4/1995 |
| JP | 8-291077 A | 11/1996 |
| JP | 10-194978 A | 7/1998 |
| JP | 11-80005 A | 3/1999 |
| JP | 11-139977 A | 5/1999 |
| JP | 2000-16942 A | 1/2000 |
| JP | 2000-336034 A | 12/2000 |
| JP | 2004-300146 A | 10/2008 |
| WO | 2004/039383 A1 | 5/2004 |
| WO | WO2006065947 | 6/2006 |
| WO | 2009/028605 A1 | 3/2009 |
| WO | 2012-051173 | 4/2012 |

OTHER PUBLICATIONS

Medline Plus: Prostatitis-Nonbacterial: Mar. 24, 2009, Online, URLhttps://web.archive.org/web/20090324022610/http://www.nlm.nih.gov/medlineplus/ency/article/000524.htm 3 pages.*
Tamaki, M APP-099 Report on Efficacy of Neurotropin for Chronic Nonbacterial Prostatis; Japanese Journal of Urology; vol. 101, No. 2, Feb. 2010.*
Makoto Tamaki, "Mansei Hi Saikinsei Zenritsusen'en ni Taisuru Neurotropin no Yukosei Hokoku", The Japanese Journal of Urology, vol. 101 No. 2, Feb. 20, 2010, p. 196 (230).
Search report from International Application PCT/JP2011/055609, mail date is Jun. 14, 2011.
Extended European Search Report of Jul. 24, 2013 for family member European Patent Application No. 11 753 428.9.

(Continued)

*Primary Examiner* — Patricia A Leith
(74) *Attorney, Agent, or Firm* — Greenblum & Bernstein, P.L.C.

(57) ABSTRACT

The purpose of the present invention is to provide a medicinal agent which is useful for amelioration or treatment of chronic prostatitis, interstitial cystitis and/or urination disorders. The present invention relates to a novel medical use of an extract from inflamed tissues inoculated with vaccinia virus, and more particularly, it relates to an ameliorating or therapeutic agent for chronic prostatitis, interstitial cystitis and/or urination disorders containing the extract as an active ingredient. The medicinal agent of the present invention containing the extract as an active ingredient is extremely useful as a highly effective and highly safe ameliorating or therapeutic agent for chronic prostatitis, interstitial cystitis and/or urination disorders.

11 Claims, No Drawings

(56) References Cited

OTHER PUBLICATIONS

Palapattu, Ganesh S., et al Epithelial Architectural Destruction is Necessary for Bone Marrow Derived Cell Contribution to Regenerating Prostate Epithelium, The Journal of Urology, vol. 176, pp. 813-818, Aug. 2006.

Informal Comments on International Search Report submitted Jul. 11, 2012 in PCT/JP2011/055609 with Certificate executed by President of the 98th Annual Meeting of the Japanese Urological Association relating to Tamaki, M APP-099 Report on Efficacy of Neurotropin for Chronic Nonbacterial Prostatitis Japanese Journal of Urology, vol. 101, No. 2, Feb. 2010, in Japanese and English Translation thereof.

\* cited by examiner

AMELIORATING OR THERAPEUTIC AGENT FOR CHRONIC PROSTATITIS, INTERSTITIAL CYSTITIS AND/OR URINATION DISORDERS

TECHNICAL FIELD

The present invention relates to a novel medical use of an extract from inflamed tissues inoculated with vaccinia virus and, more particularly, it relates to an ameliorating or therapeutic agent for chronic prostatitis, interstitial cystitis an/or urination disorders containing an extract from inflamed tissues inoculated with vaccinia virus as an active ingredient.

BACKGROUND ART

Prostatitis syndrome includes prostatitis by various pathologies and is a urological disease found in male adults in a relatively high frequency. Formerly, this disease was classified into acute bacterial prostatitis, chronic bacterial prostatitis, chronic nonbacterial prostatitis and prostatodynia (Drach et al., 1978) but, at present, the disease type classification newly proposed in 1999 by the National Institute of Health (NIH) has been widely used (Krieger, et al.). According to the new classification, prostatitis syndrome is classified into four groups of category I (acute bacterial prostatitis), category II (chronic bacterial prostatitis; CBP), category III (chronic prostatitis/chronic pelvic pain syndrome; CP/CPPS) (sometimes called chronic intrapelvic pain syndrome/prostate-related pain syndrome)) and category IV (asymptomatic inflammatory prostatitis). The correlation between old and new classifications is that acute bacterial prostatitis in the old classification corresponds to the category I of the new classification, chronic bacterial prostatitis in the old classification corresponds to the category II of the new classification and chronic nonbacterial prostatitis and prostatodynia in the old classification are integrated by the category III of the new classification. Further, in the category III, there are inflammatory one (category IIIA) and non-inflammatory one (category IIIB). Category IV of the new classification has no corresponding old classification and is a newly established one.

When there is just mentioned "chronic prostatitis" in the present application, it covers the category II (CBP) and the category III (CP/CPPS) in the above new classification. Although both have common symptom, it has been said that, in terms of frequency, the category III is far more than the category II.

On the other hand, there is interstitial cystitis (IC) which is a disease showing a lower urinary tract symptom such as frequent urination. This disease is mostly found in females and it has been said to be rare in males. As to chronic prostatitis (category III), there are reports that 60% thereof shows petechial hemorrhage due to hydrodistention of the bladder under anesthetization and that 84% of the case is positive in a potassium test which is a test for hyperpermeability of urothelium whereby the correlation to and overlap with interstitial cystitis is predicted.

Symptoms

In chronic prostatitis, pain of hypogastrium corresponding to perineal region, penis, scrotum or bladder, pain of pelvis such as ejaculatory pain or indefinite complaint such as urination disorder including micturition pain, residual urine, frequent urination or the like are typical symptoms. For judging the severity of chronic prostatitis and the therapeutic effect of the drug, there has been used the NIH Chronic Prostatitis Symptom Index (NIH-CPSI) which is stipulated by the NIH and is constituted of the question form for three domains, i.e. Pain or Discomfort, Urination and Quality of life (QOL).

On the other hand, in interstitial cystitis, interstitium results in inflammation and muscle of bladder shrinks. Therefore, bladder does not swell and urine only in an amount of not more than one half of normal bladder is able to be stored whereby the lower urinary tract symptom such as frequent urination, increased desire to urinate, urinary urgency or bladder pain is resulted. As mentioned above, there are many cases where chronic prostatitis (category III) and interstitial cystitis are unable to be discriminated by subjective symptom or urinary observation and they are often overlapped. Therefore, there are many cases where a patient is diagnosed as chronic prostatitis in spite of the fact that he/she is with interstitial cystitis or, conversely, a patient being initially diagnosed as chronic prostatitis is finally diagnosed as interstitial cystitis.

Therapy

Since there is a possibility that bacterial infection is a cause of the category II of chronic prostatitis, antibacterial chemotherapy is a main therapeutic method. Actually however, there are many cases which are resistant to the therapy and it is often that continuance of or change in antibacterial agent is necessary or that the following therapeutic agent for the category III is used together therewith.

On the other hand, with regard to the category III, the cause of its onset is still ambiguous even at present and there is no definite therapeutic method. Accordingly, in the therapy of the category III, abundant and various therapeutic methods are tried with a presumption that various causes and pathologies such as retention of prostatic fluid, participation of autoimmune or allergy, participation of mycoplasma or chlamydia, imbalance of sexual hormones or psychological factor are in the background. Examples thereof include the therapy using various medicaments such as antibacterial agent (newquinolone type and tetracycline type), al blocker (tetrazocine, tamsulosin and alfuzosin), plant preparation (cernitin pollen extract), nonsteroidal anti-inflammatory drugs [NSAIDs] (celecoxib), anti-anxiety agent (diazepam) or Chinese herbal medicine; massage of prostate; thermotherapy; acupuncture; and microwave therapy via urinary tract. However, the efficacy rate in any of them is said to be about 50 to 60%.

In the category III, there are the cases where a plurality of factors are complicated or where transfer from the category II to the category III takes place whereby symptom and therapy of the category III become more complex. As such, chronic prostatitis (categories II and III) is a long-sustaining intractable disease showing resistance to various therapies and is the disease having many clinical problems. In view of the current status as mentioned above, there has been a strong demand from the actual clinical fields for the medicament which is effective for chronic prostatitis.

On the other hand, interstitial cystitis is also a disease where the cause has not been clarified yet. Since it is not resulted by bacteria, antibiotic substances are ineffective. The therapy therefor is usually conducted by combining several means such as hydrodistention of the bladder, intravesical instillation of dimethyl sulfoxide (DMSO) or drug therapy. As to the medicament, antidepressant, antihistaminic agent, etc. are used. Object of the therapy is not to completely cure but its target is alleviation/disappearance of the symptom.

The extract from inflamed tissues inoculated with vaccinia virus as an active ingredient in the ameliorating or therapeutic agent for chronic prostatitis, interstitial cystitis an/or urination disorders of the present invention (hereinafter referred to as "the medicinal agent of the present invention") is disclosed to have the following effects: an analgesic effect, sedative effect, anti-stress effect and anti-allergic effect (see Patent Document 1); an immunostimulating effect, anti-cancer effect and cirrhosis inhibitory effect (see Patent Document 2); a treatment effect against idiopathic thrombocytopenic purpura (see Patent Document 3); a treatment effect against postherpetic neuralgia, brain edema, dementia, spinocerebellar degeneration and the like (see Patent Document 4); a treatment effect against Raynaud syndrome, diabetic neuropathy, sequelae of subacute myelo-optico-neuropathy and the like (see Patent Document 5); a kallikrein production inhibitory effect and peripheral circulatory disorder improving effect (see Patent Document 6); a bone atrophy improving effect (see Patent Document 7); a nitric oxide production inhibitory effect effective for the treatment of sepsis and endotoxic shock (see Patent Document 8); a treatment effect against osteoporosis (see Patent Document 9); a treatment effect against AIDS based on a Nef action inhibitory effect and chemokine production inhibitory effect (Patent Documents 10 and 11); a treatment effect against ischemic disorders such as cerebral infarction (Patent Document 12); a treatment effect against fibromyalgia syndrome (Patent Document 13); and a treatment effect against infections (Patent Document 14); prophylactic or alleviating effect for a peripheral nerve disorder induced by an anti-cancer agent and the like. However, it is not known that the extract from inflamed tissues inoculated with vaccinia virus as an active ingredient in the medicinal agent of the present invention is effective for amelioration or therapy of chronic prostatitis, interstitial cystitis an/or urination disorders.

PRIOR ART DOCUMENTS

Patent Documents

Patent Document 1: Japanese Patent Laid-Open No. Sho-53-101515
Patent Document 2: Japanese Patent Laid-Open No. sho-55-87724 (pages 3, 5 and 6)
Patent Document 3: Japanese Patent Laid-Open No. Hei-1-265028 (pages 1 and 2)
Patent Document 4: Japanese Patent Laid-Open No. Hei-1-319422 (pages 3 and 4)
Patent Document 5: Japanese Patent Laid-Open No. Hei-2-28119 (page 3)
Patent Document 6: Japanese Patent Laid-Open No. Hei-7-97336 (page 4)
Patent Document 7: Japanese Patent Laid-Open No. Hei-8-291077
Patent Document 8: Japanese Patent Laid-Open No. Hei-10-194978
Patent Document 9: Japanese Patent Laid-Open No. Hei-11-80005 (pages 2 and 3)
Patent Document 10: Japanese Patent Laid-Open No. Hei-11-139977
Patent Document 11: Japanese Patent Laid-Open No. 2000-336034 (pages 2 and 3)
Patent Document 12: Japanese Patent Laid-Open No. 2000-16942
Patent Document 13: International Publication No. WO 2004/039383
Patent Document 14: Japanese Patent Laid-Open No. 2004-300146
Patent Document 15: International Publication No. WO2009/028605

SUMMARY OF THE INVENTION

Problems to be Solved by the Invention

An object of the present invention is to provide a medicinal agent which is effective for amelioration or therapy of chronic prostatitis, interstitial cystitis and/or urination disorder and has high safety.

Means for Solving the Problems

The present inventors have conducted intensive studies for a drug therapy of chronic prostatitis and interstitial cystitis for which effective therapeutic method has been demanded and, as a result, they have found that an extract from inflamed tissues inoculated with vaccinia virus shows excellent ameliorating or therapeutic effect for chronic prostatitis, interstitial cystitis and/or urination disorder and achieved the present invention.

Advantages of the Invention

The extract from inflamed tissues inoculated with vaccinia virus has an excellent pharmacological action that it ameliorates or treats chronic prostatitis, interstitial cystitis and/or urination disorder. Moreover, the medicinal agent of the present invention containing said extract as an active ingredient is a safe medicinal agent having little problem such as side effect and is very highly useful.

MODE FOR CARRYING OUT THE INVENTION

The present invention relates to an ameliorating or therapeutic agent for chronic prostatitis, interstitial cystitis and/or urination disorder containing an extract from inflamed tissues inoculated with vaccinia virus as an active ingredient. As mentioned above, although various therapeutic methods have been attempted for the therapy of chronic prostatitis partly due to the fact that the etiology has not been clarified yet, efficacy in any of them has been said to be about 50 to 60%. Therefore, it has been adopted as the base that a therapeutic method by which efficacy is expected is firstly conducted for 4 to 6 weeks as one course and, if that is found to be ineffective, other therapy is conducted.

Further, for the therapy of interstitial cystitis, various therapeutic methods such as hydrodistention of the bladder or intravesical instillation of DMSO have been carried out. Since the suitable therapeutic method varies depending upon each patient as such, the medicinal agent of the present invention is useful as one of the choices in various therapeutic methods for chronic prostatitis and interstitial cystitis and is also able to be appropriately used together with other therapeutic method.

As for the extract from inflamed tissues inoculated with vaccinia virus, there are various reports on physiological active substances produced in the inflamed tissues inoculated with vaccinia virus, the method for extracting the substances from the diseased tissues, the pharmacological activities and the like as mentioned above (for example, Patent Documents 1 to 15).

Furthermore, a preparation of an extract from inflamed skins of rabbits inoculated with vaccinia virus is a commercially available pharmaceutical product which is available for the medicinal agent of the present invention. The preparation, as described in pages 2978 to 2980 of "Drugs in Japan, Ethical Drugs" (2010, edited and published by Japan Pharmaceutical Information Center), contains non-proteinous active substances extracted and separated from the inflamed skin tissues of rabbits inoculated with vaccinia virus. The preparation is known to be effective against low back pain, cervicobrachial syndrome, symptomatic neuralgia, periarthritis scapulohumeralis, osteoarthritis, itchiness accompanied with skin diseases (eczema, dermatitis, urticaria), allergic rhinitis, sequelae of subacute myelo-optico-neuropathy such as coldness, paresthesia and pain, postherpetic neuralgia and the like. The preparation is approved as an ethical drug in the form of hypodermic, intramuscular and intravenous injection products and of tablets and is commercially available.

Hereinafter, the process for producing the extract of inflamed tissues inoculated with vaccinia virus as an active ingredient in the medicinal agent of the present invention and the like will be described.

The extract from inflamed tissues inoculated with vaccinia virus used in the medicinal agent of the present invention can be obtained by the following manner: inflamed tissues inflamed by the inoculation with vaccinia virus is crushed; an extraction solvent is added to remove the tissue fragments; then deproteinization is carried out; the deproteinized solution is adsorbed onto an adsorbent; and then the active ingredient is eluted.

The extract from inflamed tissues inoculated with vaccinia virus is produced, for example, according to the following process.

(a) Inflamed skin tissues of rabbits, mice or the like by the inoculation with vaccinia virus are collected, and the inflamed tissues are crushed. To the crushed tissue an extraction solvent such as water, phenolated water, physiological saline or phenol-added glycerin water is added. Then, the mixture is filtered or centrifuged to obtain an extraction liquid (filtrate or supernatant).

(b) The pH of the extraction liquid is adjusted to be acidic and the liquid is heated for deproteinization. Then, the deproteinized solution is adjusted to be alkaline, heated, and then filtered or centrifuged.

(c) The obtained filtrate or supernatant is made acidic and adsorbed onto an adsorbent such as activated carbon or kaolin.

(d) To the adsorbent, an extraction solvent such as water is added, the pH is adjusted to alkaline, and the adsorbed component is eluted to obtain the extract from inflamed tissues inoculated with vaccinia virus. Subsequently, as desired, the eluate may be evaporated to dryness under reduced pressure or freeze-dried to give a dried material.

As for animals in order to obtain the inflamed tissues by the inoculation of vaccinia virus, various animals that is infected with vaccinia virus such as rabbits, cows, horses, sheep, goats, monkeys, rats or mice can be used, and preferred inflamed tissues are inflamed skin tissues of rabbits.

The inflamed tissues are collected and crushed, and 1 to 5 volumes of extraction solvent is added to make an emulsified suspension. As for the extraction solvent, distilled water, physiological saline, weakly acidic to weakly basic buffer and the like can be used, and stabilizers such as glycerin, antibacterial/antiseptic agents such as phenol, and salts such as sodium chloride, potassium chloride or magnesium chloride may be suitably added. At this time, the extraction may be facilitated by breaking the cellular tissues with treatment such as freezing and thawing, ultrasonic waves, cell membrane dissolving enzymes or surfactants.

The obtained emulsified extraction liquid is subjected to filtration, centrifugation or the like to remove tissue fragments, and then deproteinized. The deproteinization operation may be carried out by a generally known method, for example, heat treatment, treatment with a protein denaturant such as an acid, base, urea and guanidine, treatment with an organic solvent such as acetone, isoelectric precipitation, and salting out can be applied. Then, by a general method for removing insolubles such as filtration using filter paper (for example, cellulose or nitrocellulose), glass filters, Celite, Seitz filters or the like, ultrafiltration and centrifugation, the precipitated insoluble protein is removed.

The extraction liquid containing active ingredients obtained in this manner is acidified, preferably adjusted to pH 3.5 to 5.5 with an acid such as hydrochloric acid, sulfuric acid or hydrobromic acid, and then adsorbed onto an adsorbent. Examples of the usable adsorbent include activated carbon and kaolin. The adsorbent may be added into the extraction liquid to stir, or the extraction liquid may be passed through a column filled with the adsorbent to adsorb the active ingredients onto the adsorbent. When the adsorbent is added into the extraction liquid, the solution is removed by filtration, centrifugation, or the like to obtain the adsorbent in which the active ingredients are adsorbed.

In order to elute (desorb) the active ingredients from the adsorbent, an elution solvent is added to the adsorbent to elute at room temperature or with suitable heating or with stirring, and the adsorbent is removed by a general method such as filtration, centrifugation, or the like. As for the elution solvent to be used, a basic solvent such as water, methanol, ethanol or isopropanol that are adjusted to have a basic pH or a suitable mixture thereof may be used, and preferably water adjusted to pH 9 to 12 may be used.

The extract (eluate) obtained in this manner may be properly prepared in a suitable form as a raw material for a formulation or a pharmaceutical formulation. For example, the solution may be adjusted to have nearly neutral pH to be a raw material for a formulation, and may be adjusted to have a desired concentration by concentration or dilution. In addition, for a formulation for injection, sodium chloride may be added to prepare a solution isotonic to physiological saline. Furthermore, the solution may be concentrated to dryness or freeze-dried to prepare a solid form available for the raw material of tablets or the like.

Examples of an administration method to a patient include oral and other administrations such as subcutaneous, intramuscular and intravenous administrations. The dose can be suitably determined depending on the type of extract from inflamed tissues inoculated with vaccinia virus. The dose that is approved in the commercially available preparation according to the "Drugs in Japan, Ethical Drugs" (page 2978) is principally 16 NU per day by oral administration and 3.6 to 7.2 NU per day by injection. However, the dose may be appropriately increased or decreased depending on the type of disease, degree of seriousness, individual difference in the patients, method of administration, period of administration and the like (NU: Neurotropin unit. Neurotropin unit is defined by $ED_{50}$ value of analgesic effect measured by a modified Randall-Selitto method using SART-stressed mice that are chronic stressed animals showing a lowered pain threshold than normal animals. One NU indicates the activity of 1 mg of analgesic ingredients in Neurotropin preparations when the $ED_{50}$ value is 100 mg/kg of the preparation).

Hereinafter, examples of methods for producing an extract from inflamed tissues inoculated with vaccinia virus as well as clinical evaluation concerning novel pharmacological activity of the extract, that is, the ameliorating and therapeutic action for chronic nonbacterial prostatitis and interstitial cystitis, are described. The present invention is not intended to be limited to the descriptions in Examples.

EXAMPLES

Example 1

Skins of healthy adult rabbits were inoculated with vaccinia virus. The inflamed skins were removed and crushed, and to the crushed skins, phenolated water was added. Then, the mixture was filtered under pressure, and the obtained filtrate was adjusted to pH 5 with hydrochloric acid, and then heated at 90 to 100° C. for 30 minutes. After deproteinization by filtration, the filtrate was adjusted to pH 9 with sodium hydroxide, further heated at 90 to 100° C. for 15 minutes, and then filtered. The filtrate was adjusted to about pH 4.5 with hydrochloric acid, and 2% activated carbon was added. The mixture was stirred for 2 hours and then centrifuged. To the collected activated carbon, water was added. The mixture was adjusted to pH 10 with sodium hydroxide, stirred at 60° C. for 1.5 hours, and then centrifuged and filtered to obtain a supernatant. To the collected activated carbon, water was added again. The mixture was adjusted to pH 11 with sodium hydroxide, stirred at 60° C. for 1.5 hours, and then centrifuged to obtain a supernatant. The two supernatants were combined and neutralized with hydrochloric acid to obtain an extract from inflamed skins of rabbits inoculated with vaccinia virus.

Example 2

Skins of healthy adult rabbits were inoculated with vaccinia virus to be infected. Subsequently, the inflamed skins were aseptically removed and chopped, and then phenol-added glycerin water was added. The mixture was ground with a homogenizer to be emulsified. Subsequently, the emulsion was filtered. The obtained filtrate was adjusted to weak acidity (pH 4.5 to 5.5) with hydrochloric acid, then heated at 100° C. and filtered. The filtrate was adjusted to weak alkalinity (pH 8.5 to 10.0) with sodium hydroxide, further heated at 100° C. and then filtered. The filtrate was adjusted to about pH 4.5 with hydrochloric acid, and about 1.5% activated carbon was added. The mixture was stirred for 1 to 5 hours and then filtered. To the activated carbon collected by the filtration, water was added. The mixture was adjusted to pH 9.4 to 10 with sodium hydroxide, stirred for 3 to 5 hours, and then filtered. The filtrate was neutralized with hydrochloric acid.

Example 3

Skins of healthy adult rabbits were inoculated with vaccinia virus to be activated. Then the activated skins were aseptically removed and chopped, and water was added. The mixture was ground with a homogenizer to be emulsified. Subsequently, the emulsion was filtered under pressure. The obtained filtrate was adjusted to pH 5.0 with hydrochloric acid, and then heated at 100° C. with flowing steam. After deproteinization by filtration, the filtrate was adjusted to pH 9.1 with sodium hydroxide, further heated at 100° C. and then filtered. The filtrate was adjusted to pH 4.1 with hydrochloric acid, and 2% activated carbon was added. The mixture was stirred for 2 hours and then filtered. To the filtrate, 5.5% activated carbon was further added, and the mixture was stirred for 2 hours and then filtered. To the activated carbon collected by the former filtration, water was added. The mixture was adjusted to pH 9.9 with sodium hydroxide, stirred at 60° C. for 1.5 hours, and then filtered. To the former activated carbon and the latter activated carbon, water was added. The mixture was adjusted to pH 10.9 with sodium hydroxide, stirred at 60° C. for 1.5 hours, and then filtered. The filtrates were combined and neutralized with hydrochloric acid. Then, the filtrate was desalted by electrodialysis using a membrane with a molecular weight of 100, and dried under reduced pressure.

Now there will be shown an example of the results of clinical evaluation concerning the ameliorating and therapeutic action for (1) chronic prostatitis and (2) interstitial cystitis where the extract from inflamed tissues inoculated with vaccinia virus of the present invention prepared in the above Example 1 was used as a test drug.

(1) Clinical Evaluation for Chronic Prostatitis According to the Japanese Version of the NIH-CPSI In order to check the effect of the medicinal agent of the present invention (an extract from inflamed skin inoculated with vaccinia virus prepared in Example 1) to chronic prostatitis, a clinical evaluation in accordance with the NIH-CPSI was conducted as follows.

Forty-nine cases of the patients newly diagnosed as the category III of prostatitis syndrome (chronic non-bacterial prostatitis according to the old classification) were orally and daily administered with "Neurotropin Tablets (4 Units)" (trade name of the oral preparation which is the medicinal agent according to the present invention) as a test drug (two tablets for each time and the administration is done twice daily). Basically, no other drug was used together. At the stages of before starting the administration and after two and six weeks from the administration, inquiries according to the NIH-CPSI (Japanese version) were done to the patients. The inquiries according to the NIH-CPSI are roughly classified into three domains being constituted from total scores for 9 items in total comprising 4 items concerning pain or discomfort (items 1 to 4; total score: 0 to 21 point(s)), 2 items concerning urination symptoms (feeling of residual urine and frequent urination) (items 5 to 6; total score: 0 to 10 point(s)) and 3 items concerning a lowering of QOL (items 7 to 9; total score: 0 to 12 point(s)) and the higher the score, the severer the symptom. Mean value of total score for each domain and that of total score for all items were calculated respectively and the values of before and after the administration of the test drug were compared to evaluate the clinical effect of the medicinal agent of the present invention. In comparing the scores before and after the administration of the test drug, a paired t-test was used for testing the significant difference. As to the Japanese version of the NIH-CPSI, there was used the version which is the same as that mentioned in page 59 of "Japan Medical Journal", No. 4463 (Nov. 7, 2009). With regard to the case numbers, there is one more case only for the evaluating item for pain or discomfort and that is because the patient with this case replied only for the evaluating item of pain or discomfort. Result of the above clinical evaluation is shown in Table 1.

TABLE 1

| Evaluating Items | Questionnaire Date | Before Administration | Two Weeks after Administration | Before Administration | Six Weeks after Administration |
|---|---|---|---|---|---|
| Pain or Discomfort | Case Numbers | 49 cases | | 28 cases | |
| | Average Scores | 9.7 | 5.2 | 9.6 | 4.3 |
| | Difference in Average Scores before and after Administration | −4.5 | | −5.3 | |
| | P Values | P < 0.0001 | | P < 0.0001 | |
| Urination | Case Numbers | 48 cases | | 27 cases | |
| | Average Scores | 4.1 | 2.3 | 4.0 | 1.9 |
| | Difference in Average Scores before and after Administration | −1.8 | | −2.1 | |
| | P Values | P < 0.0001 | | P = 0.0007 | |
| QOL | Case Numbers | 48 cases | | 27 cases | |
| | Average Scores | 7.8 | 5.4 | 7.6 | 4.0 |
| | Difference in Average Scores before and after Administration | −2.4 | | −3.6 | |
| | P Values | P < 0.0001 | | P < 0.0001 | |
| Total of 3 Items (Pain or Discomfort; Urination; and QOL) | Case Numbers | 48 cases | | 27 cases | |
| | Average Scores | 21.5 | 13.0 | 21.3 | 10.4 |
| | Difference in Average Scores before and after Administration | −8.5 | | −10.9 | |
| | P Values | P < 0.0001 | | P < 0.0001 | |

As will be apparent from the above Table 1, total scores for all items of the NIH-CPSI significantly decreased when the medicinal agent of the present invention was administered to the patients suffering from chronic prostatitis. Since the medicinal agent of the present invention significantly decreased the average scores of each three domains of pain or discomfort, urination symptom and lowering in QOL according to the NIH-CPSI, it has been shown that the medicinal agent ameliorates the symptom of chronic prostatitis as a whole and is an effective therapeutic agent for this disease. With regard to the administering period of the medicinal agent of the present invention, scores of the NIH-CPSI decreases by the administration for two weeks whereby a sufficient therapeutic effect was noted while, for the patients subjecting to the administration of continued six weeks in total, it was shown that the NIH-CPSI scores further decreased and efficacy was enhanced. Moreover, no side effect was noted in all of the cases.

With regard to tamsulosin (al blocker), levofloxacin (an antibacterial agent), NSAIDs and cernitin pollen extract (a plant preparation), which are currently administered as the therapeutic agent for category III, there is a literature report where their therapeutic effects were evaluated according to the NIH-CPSI the same as in the above clinical evaluation. Even when compared with those results, the medicinal agent of the present invention has been found to have better ameliorating or therapeutic effect for the category III.

(2) Clinical Evaluation for Interstitial Cystitis According to the Japanese Version of the Questionnaire about O'Leary and Sant Interstitial Cystitis Symptom and Problem Index "Neurotropin Tablets (4 units)" were orally administered daily as a test drug to four cases being diagnosed as interstitial cystitis (Two tablets at a time and the administration was done twice daily). Basically, neither other medicament nor other therapeutic method was applied together therewith. As to a yardstick for evaluating the symptom of a patient diagnosed as interstitial cystitis, a questionnaire about O'Leary and Sant Interstitial Cystitis Symptom and Problem Index has been most widely used and the appropriateness for its Japanese version has been already checked as well. Under such circumstances, patients were asked to fill in the questionnaire before and after the administration of the medicinal agent of the present invention. The questionnaire consists of four questions for the symptom [symptom score: IC Symptom Index] (total score: 0 to 20 point(s)) and four questions for the problem noted by the symptom [problem score: IC Problem Index] (total score: 0 to 16 point (s)) and the higher the score, the severer the symptom. Total scores were calculated from each of symptom score and problem score for each of the cases and the clinical effect of the medicinal agent of the present invention was evaluated by comparing the values before and after the administration of the test drug. With regard to the Japanese version of the questionnaire about O'Leary and Sant Interstitial Cystitis Symptom and Problem Index, we used the version which is the same as that mentioned in "Clinical Guideline for Interstitial Cystitis" (First Edition; edited by the Committee for Preparing the Guideline, The Society of Interstitial Cystitis of Japan and published by Blackwell Publishing KK). Results of the above clinical evaluation are shown in Table 2.

TABLE 2

| Case No. | | | Symptom Score | | Problem Score | |
|---|---|---|---|---|---|---|
| | | | Before Administration | After 18 Days from Administration | Before Administration | After 18 Days from Administration |
| 1 | Questionnaire Date | Total Scores | 3 | 1 | 0 | 0 |
| | | Difference in Total Scores before and after Administration | | −2 | | 0 |

TABLE 2-continued

| Case No. | | Symptom Score | | | Problem Score | | |
|---|---|---|---|---|---|---|---|
| 2 | Questionnaire Date | Before Administration | After 6 Weeks from Administration | | Before Administration | After 6 Weeks from Administration | |
| | Total Scores | 3 | 3 | | 7 | 2 | |
| | Difference in Total Scores before and after Administration | | 0 | | | −5 | |
| 3 | Questionnaire Date | Before Administration | After 16 Days from Administration | | Before Administration | After 16 Days from Administration | |
| | Total Scores | 12 | 1 | | 5 | 1 | |
| | Difference in Total Scores before and after Administration | | −11 | | | −4 | |
| 4 | Questionnaire Date | Before Administration | After 6 Weeks from Administration | After 12 Days from Administration | Before Administration | After 6 Weeks from Administration | After 12 Days from Administration |
| | Total Scores | 4 | 3 | 1 | 3 | 3 | 0 |
| | Difference in Total Scores before and after Administration | | −1 | −3 | | 0 | −3 |
| 5 | Questionnaire Date | Before Administration | After 4 Weeks from Administration | | Before Administration | After 4 Weeks from Administration | |
| | Total Scores | 16 | 11 | | 12 | 11 | |
| | Difference in Total Scores before and after Administration | | −5 | | | −1 | |

As shown in the above Table 2, each of the total scores of the symptom score and/or the problem score of the questionnaire about O'Leary and Sant Interstitial Cystitis Symptom and Problem Index decreased when the medicinal agent of the present invention was administered to the patients suffering from interstitial cystitis. In the four questions for the symptom score, questions 1 to 3 relate to urination disorder such as frequent urination or increased desire to urinate and particularly significant amelioration of from 3 to 1 in the case 1, from 8 to 1 in the case 3, from 4 to 1 in the case 4 (administration for 12 weeks) and from 13 to 8 in the case 5 was noted in terms of total score of questions 1 to 3. Further, in the case 4, it was shown that the effect became high when the medicinal agent of the present invention is continuously administered for a long period. Since the total score in the questionnaire decreased by administration of the medicinal agent of the present invention as such, it has been shown that the medicinal agent of the present invention is an effective ameliorating or therapeutic agent for interstitial cystitis. Incidentally, no side effect was noted in all of the cases.

INDUSTRIAL APPLICABILITY

As will be apparent from the above evaluation for the clinical effect, it has been noted that the medicinal agent of the present invention has an excellent ameliorating or therapeutic effect for the symptoms as a whole of chronic prostatitis and/or interstitial cystitis. Further, since the effect for ameliorating the urination disorder which is the main symptom for chronic prostatitis and interstitial cystitis was also noted, it has been shown that the medicinal agent of the present invention is also useful as an ameliorating or therapeutic agent for urination disorder. A commercially available extract from inflamed skin inoculated with vaccinia virus has been used for many years and has been recognized to be a medicinal agent having very high safety. In the above clinical evaluation, no side effect was noted in all of the cases as well. As such, the medicinal agent of the present invention is effective as an ameliorating or therapeutic agent for chronic prostatitis, interstitial cystitis and/or urination disorder and is very highly useful with high safety and few side effects.

The invention claimed is:

1. A method for treating chronic prostatitis, interstitial cystitis, or urination disorders, comprising administering to a patient in need of such treatment a prophylactic or alleviating agent comprising, as an active ingredient, an extract from an inflamed tissue inoculated with vaccinia virus; wherein said urination disorders are caused by chronic prostatitis or interstitial cystitis.

2. A method as claimed in claim 1, wherein the inflamed tissue is a skin tissue.

3. A method as claimed in claim 1, wherein the inflamed tissue is a rabbit skin tissue.

4. A method as claimed in claim 1 wherein the prophylactic or alleviating agent is an oral preparation or an injectable preparation.

5. A method as claimed in claim 1 wherein chronic prostatitis is treated in a patient in need of such treatment.

6. A method as claimed in claim 5, wherein the inflamed tissue is a rabbit skin tissue, and the prophylactic or alleviating agent is an oral preparation or an injectable preparation.

7. A method as claimed in claim 1 wherein interstitial cystitis is treated in a patient in need of such treatment.

8. A method as claimed in claim 1, wherein the urination disorder caused by chronic prostatitis or interstitial cystitis is treated.

9. A method as claimed in claim 8 wherein the urination disorder is frequent urination or increased desire to urinate.

10. A method as claimed in claim 9, wherein the urination disorder is caused by chronic prostatitis.

11. A method as claimed in claim 9, wherein the urination disorder is caused by interstitial cystitis.

* * * * *